US010426519B2

(12) United States Patent
Courvoisier et al.

(10) Patent No.: US 10,426,519 B2
(45) Date of Patent: Oct. 1, 2019

(54) MINIMALLY INVASIVE SYSTEM FOR DYNAMIC CORRECTION OF A SPINAL DEFORMITY

(71) Applicants: UNIVERSITE GRENOBLE ALPES, Saint Martin d'Hères (FR); CENTRE HOSPITALIER UNIVERSITAIRE GRENOBLE ALPES, Tronche (FR)

(72) Inventors: Aurélien Courvoisier, Grenoble (FR); Ahmad Eid, Grenoble (FR); Jacques Griffet, Meylan (FR)

(73) Assignees: Universite Grenoble Alpes, Saint-Martin, d'Heres (FR); Centre Hospitalier Universitaire Grenoble Alpes, La Tronche (FR)

( * ) Notice: Subject to any disclaimer, the term of this patent is extended or adjusted under 35 U.S.C. 154(b) by 0 days.

(21) Appl. No.: 15/565,709

(22) PCT Filed: Apr. 13, 2016

(86) PCT No.: PCT/FR2016/050845
§ 371 (c)(1),
(2) Date: Oct. 11, 2017

(87) PCT Pub. No.: WO2016/166467
PCT Pub. Date: Oct. 20, 2016

(65) Prior Publication Data
US 2018/0070988 A1 Mar. 15, 2018

(30) Foreign Application Priority Data
Apr. 13, 2015 (FR) .................................. 15 53188

(51) Int. Cl.
*A61B 17/70* (2006.01)
*A61B 17/064* (2006.01)
(Continued)

(52) U.S. Cl.
CPC ...... *A61B 17/7022* (2013.01); *A61B 17/0642* (2013.01); *A61B 17/0682* (2013.01);
(Continued)

(58) Field of Classification Search
CPC ..... A61B 17/064–0644; A61B 17/068–07292; A61B 17/70–7046
See application file for complete search history.

(56) References Cited

U.S. PATENT DOCUMENTS 3,959,960 A * 6/1976 Santos .................... A61B 17/04
606/82
4,438,769 A * 3/1984 Pratt ................... A61B 17/0642
227/147
(Continued)

*Primary Examiner* — Nicholas J Plionis
*Assistant Examiner* — Steven J Cotroneo
(74) *Attorney, Agent, or Firm* — Harness, Dickey & Pierce, PLC (57) ABSTRACT

A minimally invasive system for dynamic correction of a spinal deformity in patients includes: a flat ligament made of synthetic material, a plurality of staples intended to be anchored on a respective vertebral body of the patient to hold the ligament against each vertebral body, and a device for mechanically tensioning the ligament. Furthermore, the device for mechanically tensioning the ligament includes a tubular rod for allowing the ligament and at least one pin capable of penetrating the vertebral body so as to prevent slippage of the distal end of the rod on the vertebral body to move between a distal end and a proximal end of the rod, leading, at the distal of the rod, into a notch suitable for the ligament to pass through, and a torque wrench arranged at the proximal end of the rod, the torque wrench including a spindle that is perpendicular to the rod and has a slit through which the ligament passes, the spindle of the wrench being suitable for being rotated so as to adjust the mechanical tension of the ligament.

14 Claims, 6 Drawing Sheets

(51) Int. Cl.
  *A61B 17/88* (2006.01)
  *A61B 17/068* (2006.01)
  *A61B 90/00* (2016.01)

(52) U.S. Cl.
  CPC ...... *A61B 17/7044* (2013.01); *A61B 17/8869* (2013.01); *A61B 2090/066* (2016.02)

(56) References Cited

U.S. PATENT DOCUMENTS

| | | | | |
|---|---|---|---|---|
| 5,425,490 | A * | 6/1995 | Goble | A61B 17/0642 227/147 |
| 6,299,613 | B1 * | 10/2001 | Ogilvie | A61B 17/0642 606/279 |
| 7,699,203 | B2 * | 4/2010 | McBride | A61B 17/064 227/175.1 |
| 2002/0055739 | A1 * | 5/2002 | Lieberman | A61B 17/70 606/263 |
| 2002/0143329 | A1 * | 10/2002 | Serhan | A61B 17/0642 623/13.11 |
| 2006/0217713 | A1 * | 9/2006 | Serhan | A61B 17/0642 606/263 |
| 2011/0106185 | A1 * | 5/2011 | Gil | A61B 17/7022 606/86 R |
| 2013/0023907 | A1 * | 1/2013 | Sterrett | A61B 17/0469 606/148 |
| 2013/0060287 | A1 * | 3/2013 | Mickiewicz | A61B 17/701 606/263 |

* cited by examiner

MINIMALLY INVASIVE SYSTEM FOR DYNAMIC CORRECTION OF A SPINAL DEFORMITY

CROSS-REFERENCE TO RELATED APPLICATIONS

This application is a National Phase Entry of International Patent Application No. PCT/FR2016/050845, filed on Apr. 13, 2016, which claims priority to French Patent Application Serial No. 1553188, filed on Apr. 13, 2015, both of which are incorporated by reference herein.

TECHNICAL FIELD

The present invention relates to a minimally invasive system for dynamic correction of a spinal deformity, such as scoliosis.

BACKGROUND

Scoliosis is a spinal deformity mechanically characterized by torsion of the vertebral column, which affects several percent of the child population. The foremost deformity of scoliosis is axial rotation. This rotation in the transversal plane induces an automatic rotation of the vertebrae in the frontal plane which results in one or more frontal curvatures of the spine. Said curvatures may be structural at the level of the pathological zone or compensatory when they aim to reduce postural imbalance.

For each scoliotic curvature, particular vertebrae may be identified:
- the apical vertebra (also called top vertebra of the curvature) is defined as being the vertebra the most lateralised and generally having the greatest axial rotation;
- the limit vertebrae are situated at the upper and lower junctional limits; they are used to calculate the Cobb angle.

The vertebrae of a curvature are deformed in the three planes in space. Wedging of the vertebrae is indicated by deformation of the vertebral body and loss of parallelism of the end plates. It is a three-dimensional phenomenon which modifies the orientation of the vertebral end plates due to an alteration of the process of vertebral growth. This deformation also affects the intervertebral discs, which can cause their premature degeneration.

Due to the close relationship between the thoracic vertebrae and the ribs, deformation of the spine leads to a modification of the orientation of the ribs and the shape of the thoracic cage. The phenomenon of torsion drags the ribs and creates a hump in the back of the patient, called gibbosity. Deformations of the thoracic cage may have a very significant impact on the respiratory function in the most severe forms of scoliosis.

Growth constitutes a determining factor in the constitution of a scoliosis. Indeed, scoliosis worsens during the period of rapid growth that peaks at puberty. Conversely, moderate scolioses remain stable after the end of growth.

There exists no curative treatment for the pathology from which scoliosis originates. The main objective of the treatment is thus to stop the aggravation of scoliosis either as a result of the residual growth potential or as a result of the structuring of compensation curvatures or the risk of secondary disc degeneration (osteoarthritis).

Conservative treatment by corset is at the present time the treatment of choice for scolioses that progress during growth. Most rigid corsets have the objective of correcting the translation of the apical vertebra in the frontal plane. They come under the principle of support—counter support. The application of a force on the apex of the main curvature makes it possible to translate the apical vertebra towards the median line. Counter supports are necessary; they are always iliac and thoracic.

The corset does not cure scoliosis because it does not make it possible to modify the deformation (the wedging) of each of the vertebrae. It acts like a supporting stake which makes it possible to avoid more serious aggravation. To be effective, the corset has to be worn 20 h/24 h until the child has stopped growing (sometimes more than 5 years). But the real effectiveness of corsets remains highly controversial. In addition, tolerance to the treatment and the psychological impact on the body image is important.

Surgical treatment is the last resort in the event of severe scoliosis. Its objective is the same as for the orthopaedic treatment, namely the stabilisation of the evolution of a scoliosis, but for more severe scolioses. Surgery consists in a correction of the deformation by means of screws, fasteners and rods and a fusion of the vertebrae together by means of a bone graft (vertebral arthrodesis). The objective of the surgical treatment is to fuse as few vertebrae together as possible in order to retain the maximum mobility in the vertebral column while restoring a satisfactory frontal and sagittal equilibrium. It is a weighty treatment associated with significant morbidity. However, conventional surgical treatment by arthrodesis cannot be envisaged for patients for whom the growth potential remains important.

Alternative methods have thus been described in animals and in humans. In humans, the technique used is convex epiphysiodesis by stapling. The idea is to block mechanically growth on the convex side of the curvature. The objective is to break the vicious circle by reducing the pressure on the concave side (corset effect) thanks to the maintaining of a correction of the stacking of the vertebrae but also to reduce wedging of the vertebrae by the effect of asymmetric blockage of growth. The technique used was initially direct stapling of the vertebrae together. However, such stapling was insufficient to correct really progressive scolioses.

Some authors have proposed using a dynamic spinal tethering device in place of staples [1]-[3]. This medical device, which is sold by the Zimmer Company under the name Dynesys™, is intended for anterior spinal tethering. This device comprises a bone anchoring screw and a synthetic ligament that connects the screws together. In publications [1]-[3], this device has been diverted from its normal indication and its effectiveness in the stabilisation or even the correction of scolioses has been evaluated. Although the results highlight the effectiveness of this device for the correction of scoliosis, several obstacles to the generalisation of its use for this indication remain. Firstly, the size of the screws is important. Indeed, once in place, the screws protrude by about 1 cm from the vertebra, which inevitably leads to rubbing on neighbouring organs, in particular the lungs. Secondly, putting in place the screws and the ligament is invasive, in so far as it requires incisions of the order of 2 to 3 cm. The result is considerable operational bleeding and a long operating time. Finally, the existing device does not make it possible to control the mechanical tension of the ligament, which is necessary to maintain the correction of the curvature.

U.S. Patent Publication No. 2013/0060287 describes a system comprising a flat ligament fixed by several vertebral implants along the vertebral column of a patient. This ligament is tensioned in the direction of its travel by means of a mechanical tensioning device which comprises, at the distal end thereof, a mechanism for driving the ligament which is actuated by a handle situated at the proximal end thereof. However, an important drawback of this device is that it has to be wedged against the vertebral implant so as not to slide on the vertebra, such that a high stress is applied to the vertebral implant during tensioning of the ligament, which is capable of tearing out or damaging the implant.

SUMMARY

An aim of the invention is to overcome the drawbacks of current systems with a view to proposing a correction system which is minimally invasive so as to minimise the duration of the intervention and the risks of per- and post-operation bleeding. This system must further make it possible to control the mechanical stress applied to the vertebrae by a ligament maintained by staples in order to ensure the effectiveness of the correction, while avoiding applying mechanical stresses to the staples during tensioning of the ligament.

In accordance with the invention, a minimally invasive system for dynamic correction of a spinal deformity in patients is proposed, characterized in that it comprises:
  a flat ligament made of synthetic material,
  a plurality of staples intended to be anchored on a respective vertebral body of the patient to hold said ligament against each vertebral body,
  a device for mechanically tensioning the ligament, said system being characterized in that the device for mechanically tensioning the ligament comprises a tubular rod allowing the ligament and at least one pin capable of penetrating the vertebral body so as to prevent slippage of the distal end of the rod on the vertebral body to pass between a distal end and a proximal end of the rod, leading, at the distal end of the rod, into a notch suitable for the ligament to pass through, and a torque wrench arranged at the proximal end of the rod, said torque wrench comprising a spindle that is perpendicular to the rod and has a slit through which the ligament passes, the spindle of the wrench being suitable for being rotated in such a way as to adjust the mechanical tension of the ligament.

In the present text, "distal" conventionally designates the end of an object intended to be inserted into the body of the patient, and "proximal" designates the end intended to be handled by the medical personnel, this end remaining outside of the body of the patient. "Correction" is taken to mean within the present text, a reduction in the spinal deformation observed prior to the implantation of the flat ligament and the staples, or at the very least a stabilisation of this deformation during growth of the patient. "Dynamic" is taken to mean within the present text that said correction takes place during growth of the patient.

In a particularly advantageous manner, each staple has two substantially parallel pointed legs having a spacing designed to provide a passage for the ligament, and a flange connecting said legs and having a tapped central orifice. Preferably, each staple further comprises, on the same side of the flange as the legs, at least one tip suited to perforate the ligament. In a particularly advantageous manner, the thickness of the flange of each staple is comprised between 1 and 3 mm.

According to a preferred embodiment, the correction system further comprises at least one pin for guiding the staple, said pin having a diameter substantially equal to the diameter of the central orifice of the staple. According to a preferred embodiment, the correction system further comprises a first device for impacting the staple, said impaction device comprising a tubular rod enabling the guiding pin to pass through said device. In a particularly advantageous manner, this first impaction device has, at the distal end thereof, an end piece suited to engage with the flange of the staple in such a way as to orient the staple in a determined position.

According to a preferred embodiment, the correction system further comprises at least one gripper for gripping the ligament, said gripper comprising two arms each having a distal end bent according to an angle comprised between 80° and 95° forming a jaw, the arms being able to be actuated between a configuration where the jaws are spaced apart and a configuration where the jaws are tightened against each other. According to a preferred embodiment, the correction system further comprises a second device for impacting the staple, said second impaction device having at the distal end thereof a retaining lug engaging with the central orifice of each staple. According to an advantageous embodiment, said retaining lug is threaded and can be screwed into the central orifice of each staple.

Furthermore, the flat ligament is typically in the form of a polyester braid. According to an advantageous embodiment, the flat ligament comprises at least one radio-opaque element extending over the entire length of said ligament. Finally, the part intended to be inserted into the body of the patient of the tensioning device, the first impaction device, the second impaction device and/or the gripper preferably has a diameter less than or equal to 10 mm.

BRIEF DESCRIPTION OF THE DRAWINGS

Other characteristics and advantages of the invention will become clear from the detailed description that follows, with reference to the appended drawings in which.

DETAILED DESCRIPTION

Figure 1A:
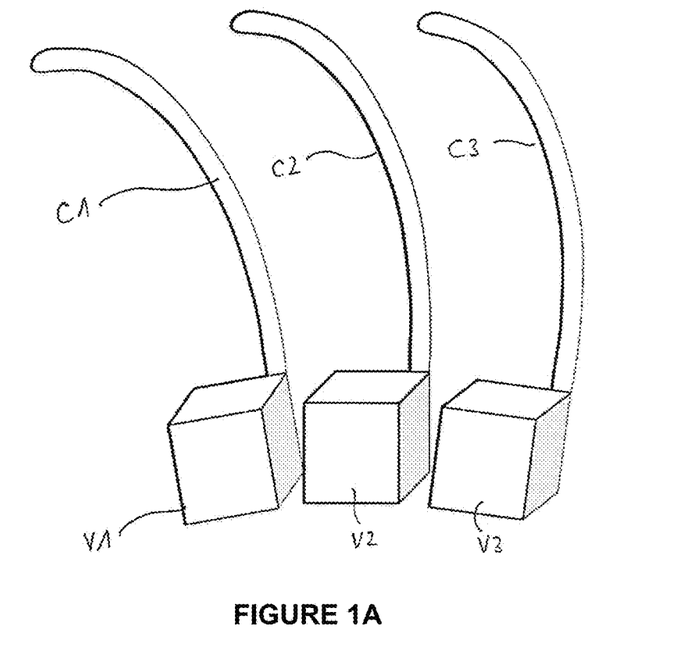
FIG. 1A is a schematic diagram of a spinal deformity to correct.
Figure 1B:
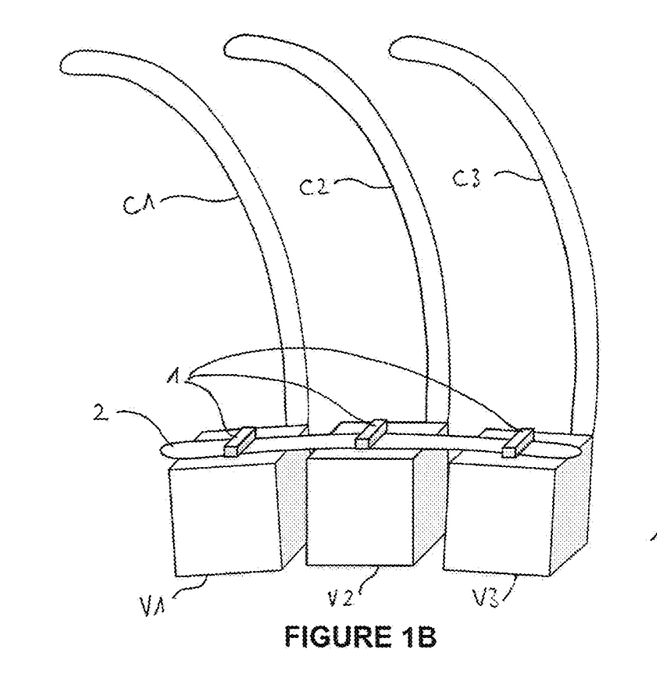
FIG. 1B is a schematic diagram of a spinal deformity corrected by means of a minimally invasive system according to the invention.

FIG. 1A is a schematic diagram of a spinal deformity to correct, in which are represented three ribs C1, C2, C3 and three respective vertebrae V1, V2, V3. Due to this deformity, the vertebra are not aligned but are arranged along a curve. FIG. 1B is a schematic diagram of said spinal deformity after correction by means of a device in accordance with the invention.

This device comprises a plurality of staples 1 (a staple being fixed on each vertebra according to a procedure which will be described in detail hereafter) and a flat ligament 2 made of synthetic material extending from one vertebra to the next and maintained in place by the staples 1. As will be explained in detail hereafter, the ligament 2 is mechanically under tension, which makes it possible to straighten the vertebrae and, if not to align them perfectly, at least to limit the curvature observed in FIG. 1A.

Figure 1C:
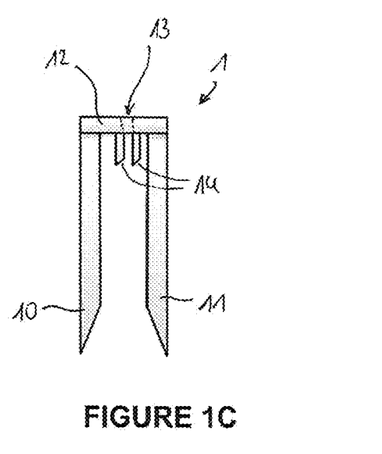
FIG. 1C is a side view of a staple forming part of such a correction system.

As illustrated in FIG. 1C, each staple 1 comprises two substantially parallel legs 10, 11 and the end of which is provided with a tip to favour the insertion of the staple in a vertebra by impaction. The two legs 10, 11 are connected by a flange 12 which has a tapped central orifice 13. The flange 12 is the only part of the staple that extends beyond each vertebra once the correction device has been put in place. The thickness of the flange 12 being typically comprised between 1 and 3 mm, the correction device does not risk interfering with neighbouring organs of the patient, notably the lungs. Thus, the correction device is clearly less cumbersome and intrusive than the screws mentioned in the preamble.

The two legs 10, 11 have a spacing designed to provide a passage for the flat ligament 2; this spacing is advantageously slightly greater than the width of the ligament. Advantageously, the staple further comprises at least one tip 14 (two are represented in FIG. 1C), situated on the same side of the flange as the legs 10, 11 and capable of perforating the ligament. This makes it possible to avoid slippage of the ligament between the legs of the staple and thereby to maintain the mechanical tension that has been imposed thereon. A staple such as that represented in FIG. 1C already exists in surgical applications different to those targeted by the present invention.

The ligament 2 is advantageously produced in the form of a braid made of biocompatible synthetic material (for example produced from polyester filaments). The width of the ligament is typically of the order of 5 to 7 mm. The thickness of the ligament is typically of the order of 0.5 to 1.5 mm. For the provided application, the ligament has a direct tensile strength greater than or equal to 1000 N.

Advantageously, the ligament is provided, at one of the ends thereof at least, with a rigid end piece, for example in the form of a metal plate, which makes it possible to handle it more easily during its insertion between the legs of the staples. According to an advantageous embodiment, the ligament may further comprise a radio-opaque element extending over its entire length. This makes it possible to visualise, on post-operation radiographs, the position and the shape of the ligament. It is thereby possible to check the effectiveness of the correction, and/or to detect a potential rupture of the ligament.

A procedure for putting in place the ligament and the staples, as well as ancillaries specially designed for this procedure, will now be described. In this procedure, the patient is positioned by the surgeon in such a way as to correct as best as possible the spinal deformity, the ligament being intended, by its mechanical tension, to maintain this correction.

Figure 2A:
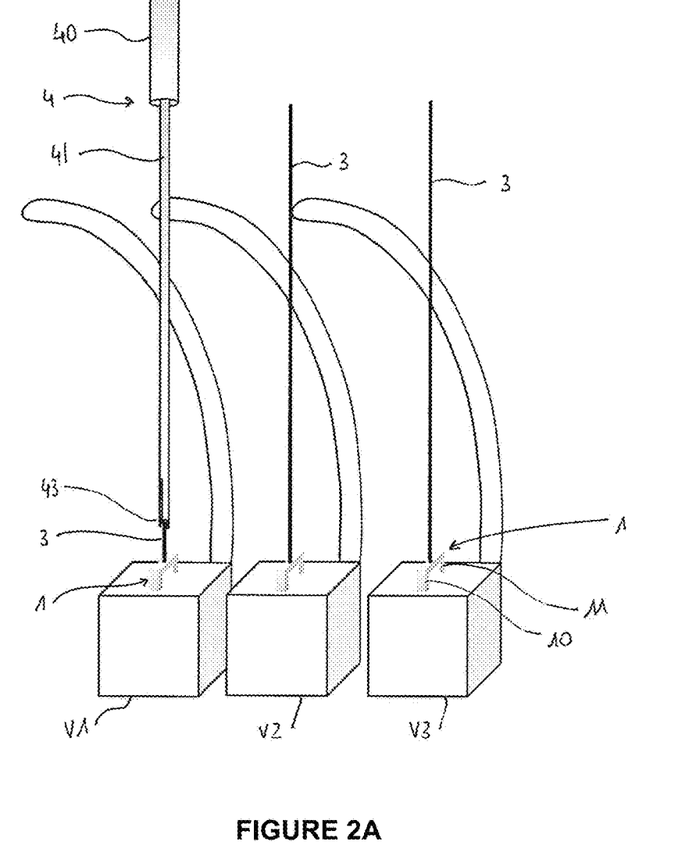
FIG. 2A is a schematic diagram of the pre-implantation of the staples in the respective vertebral bodies.

A first step comprises a pre-implantation of staples in the respective vertebral bodies. With reference to FIG. 2A, the staples 1 are put in place on each vertebra V1-V3 (the number of vertebra shown schematically here is only indicative: it goes without saying that staples may be implanted into a greater or lesser number of vertebrae as a function of the desired correction). At this stage, the tips of the staples are simply inserted into the vertebra with a limited insertion depth, in such a way as to leave, between the flange 12 and the surface of each vertebra, a sufficient height to enable the passage of the ligament later.

The putting in place of the staples is carried out by means of a pin 3, the diameter of which is substantially equal to that of the tapped orifice 13 so that the staple is well maintained by the pin. The diameter of the pin 3 is typically comprised between 2.5 and 3.2 mm. The pin has a pointed distal end making it possible to penetrate slightly into the vertebra. To put each staple in place, an incision of a few millimeters is made in the lateral part of the thorax between the ribs of the patient, the pin 3 is positioned in this opening resting on the vertebra, at the location intended for the staple, the staple is inserted on the pin 3 through the orifice 13 and the staple is made to slide up to the vertebra.

Next, a first device 4 for impacting the staple 1 is used to make the legs of the staple penetrate into each vertebra by means of a mechanical impact. As may be seen better in FIG. 2B, said impaction device 4 comprises a tubular rod 41 comprising a passage 44 for passing the pin 3 through said device, and a proximal end piece 40 intended to receive a mechanical impact applied by the practitioner. The rod 41 being intended to be inserted into the body of the patient, it has a diameter as small as possible, that is to say typically comprised between 5 and 10 mm. The end piece 40 being for its part intended to remain outside the body of the patient, it typically has a diameter bigger than that of the rod 41, that is to say for example comprised between 15 and 20 mm, in order to provide a sufficient surface for applying the impact.

Figure 2B:
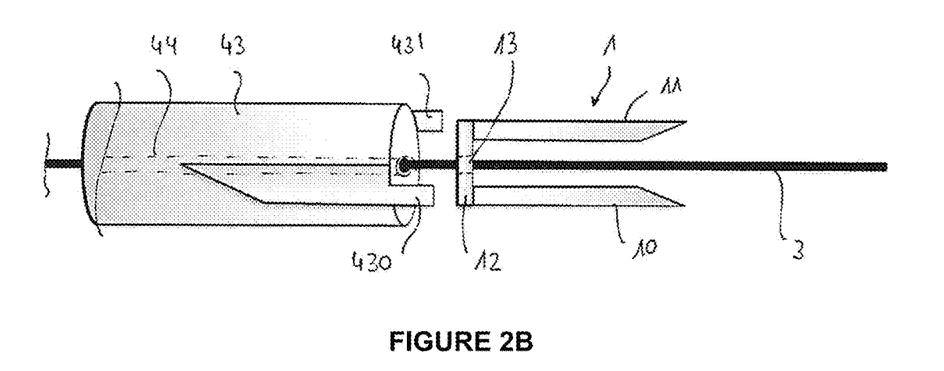
FIG. 2B is a schematic diagram of the distal end of the impaction device used during the step of FIG. 2A.

At the distal end thereof, the first impaction device 4 has an end piece 43 intended to come into contact with the flange 12 of the staple with a view to transmitting thereto the impact force applied to the proximal end piece 40. In a particularly advantageous manner, the end piece 43 is suited to engage with the flange 12 of the staple in such a way as to orient the staple in a determined position. To this end, the end piece 43 comprises two diametrically opposed arms 430, 431 extending in the distal direction, and of which the spacing is substantially equal to the width of the flange 12 of the staple. Thus, the arms 430, 431 form a means for gripping the staple which makes it possible to position it in the desired position with respect to the vertebra before and during application of the impact.

The impact force applied must be sufficiently large to make the legs of the staple penetrate into the vertebra, while being limited so that the insertion of the staple into the vertebra leaves a sufficient space to enable the insertion of the ligament between the flange and the vertebra. Once each staple thereby pre-implanted, the impaction device 4 and the pin 3 are removed.

Figure 3:
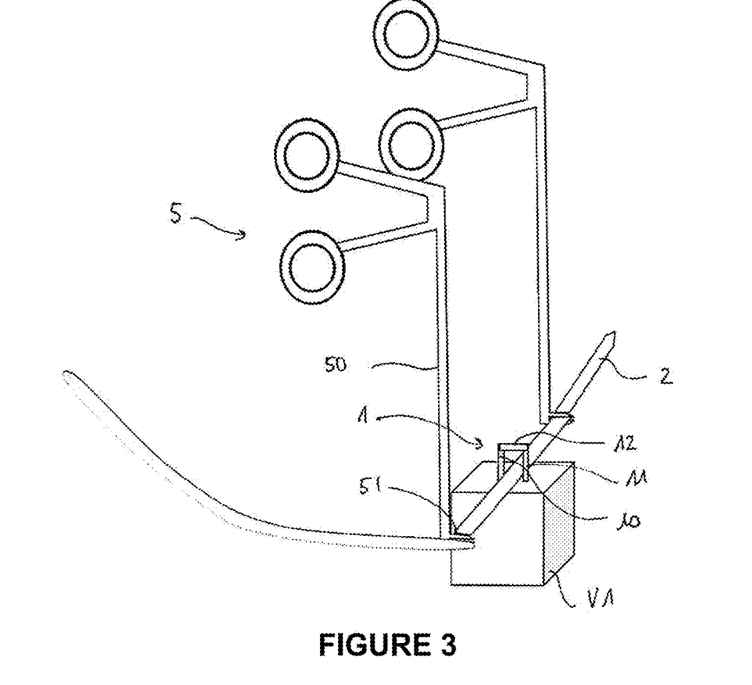
FIG. 3 is a schematic diagram of the passage of the ligament between the staples implanted in FIG. 2A.

FIG. 3 illustrates the step of inserting the flat ligament 2 between the staples pre-implanted at the preceding step. This step implements another specifically designed ancillary, namely a gripper 5 for gripping the ligament 2. Said gripper 5 comprises two arms 50 each having a distal end bent with an angle comprised between 80 and 95°, ideally equal to 90°, forming a jaw 51.

To make said gripper minimally invasive, the arms (including the jaws) are advantageously contained in a cylinder having a diameter less than 10 mm. Of course, the handles situated at the proximal end of the arms are not intended to be inserted into the body of the patient and may thus have any shape and dimension useful to good ergonomics.

The arms can be actuated between a configuration where the jaws are spaced apart (not represented here) and a configuration where the jaws are tightened against each other in such a way as to grip the ligament, as is represented in FIG. 3. It will be noted that the principle of actuation of the gripper is similar to that of disc grippers; however, unlike known gripper, in which the jaws are in the alignment of the arms, the jaws bent 90° with respect to the arms in the present invention enable easy insertion of the ligament between the staples. To this end, the jaws are placed substantially parallel to the flange of the staples and the ligament is made to slide between successive staples.

Figure 4:
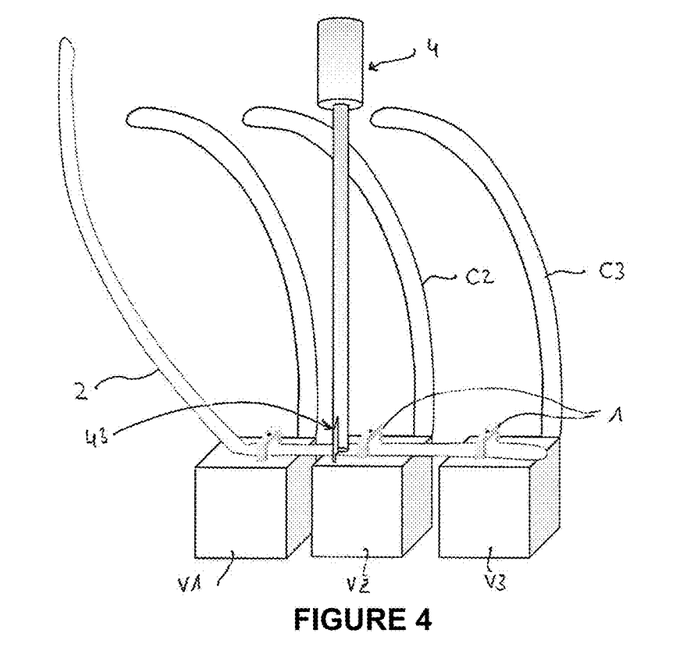
FIG. 4 illustrates in a schematic manner the use of the impaction device of FIG. 2A-2B to facilitate the passage of the ligament between the staples by pressing it against a vertebra.

In this step, the tips 14 present under the flange of the staples are liable to impede the sliding of the ligament, said ligament being able to catch onto said tips. To avoid this pitfall, the impaction device 4 described above could advantageously be used to hold the ligament against the surface of a vertebra by means of the distal end piece 43, as is represented in FIG. 4. Thus, the ligament is moved away as far as possible from the tips 14 while the ligament is passed between the staples.

Figure 5A:
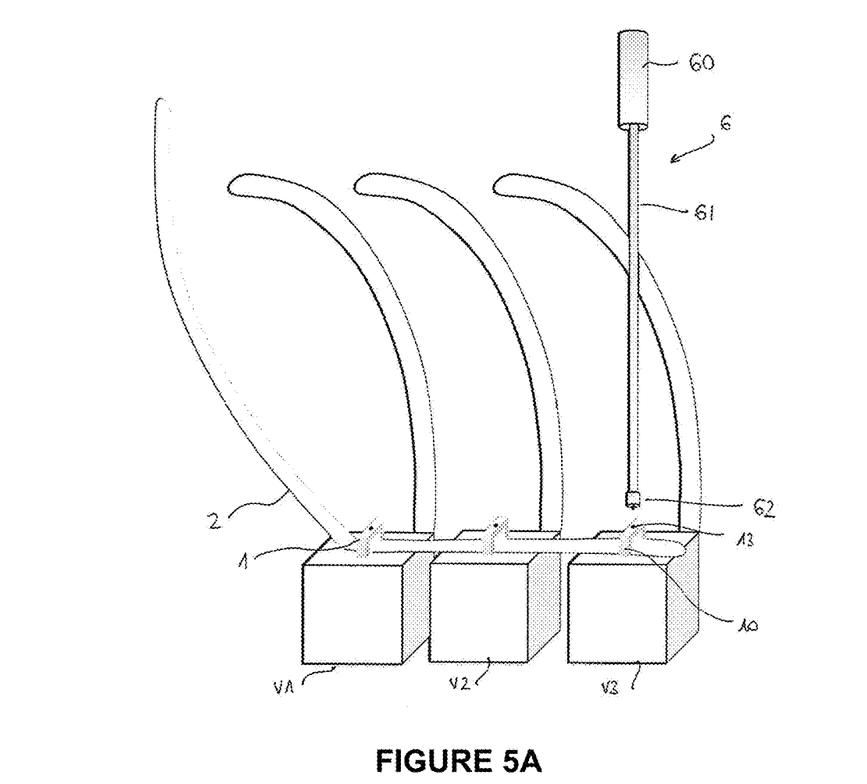
FIG. 5A is a schematic diagram of the definitive putting in place of the staples by means of a second impaction device.

Once the ligament inserted between all the staples, each staple is put in place definitively while applying a determined mechanical tension to the ligament. As illustrated in FIG. 5A, the definitive putting in place of each staple implements a second impaction device 6. Unlike the device 4, the device 6 does not need to have an internal passage because the pins 3 are no longer used at this stage of the procedure. The impaction device 6 comprises a cylindrical rod 61 and a proximal end piece 60 intended to receive a mechanical impact applied by the practitioner.

The rod 61 being intended to be inserted into the body of the patient, it has as small a diameter as possible, that is to say typically comprised between 5 and 10 mm. The end piece 60 being for its part intended to remain outside the body of the patient, it typically has a diameter greater than that of the rod 61, that is to say for example comprised between 15 and 20 mm, in order to procure a sufficient surface for applying the impact. At the distal end thereof, the impaction device 6 has an end piece 62 intended to come into contact with the flange of the staple with a view to transmitting thereto the impact force applied to the proximal end piece 60. In this step, the impact applied must be sufficiently important to drive the legs of the staple entirely into the vertebra, so as to jam the ligament between the flange and the vertebra, the ligament further being retained by the tips 14 of the staple.

Figure 5B:
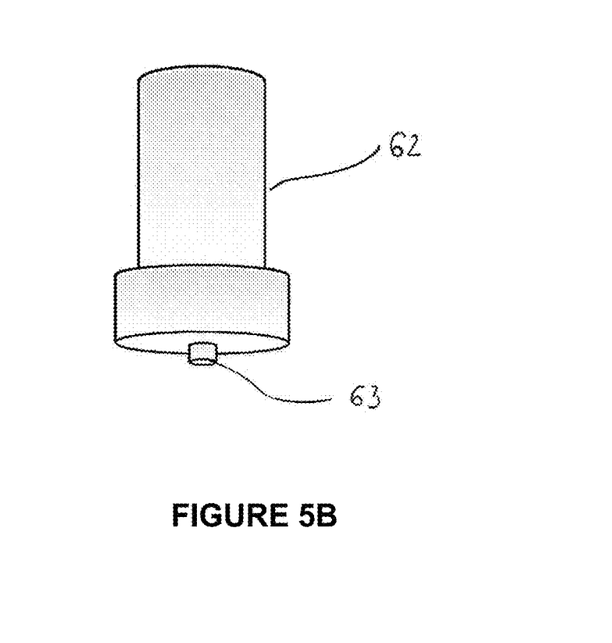
FIG. 5B is a schematic diagram of the distal end of the second impaction device.

In a particularly advantageous manner, as illustrated in FIG. 5B, the end piece 62 has a lug 63 engaging with the central orifice 13 of the staple to temporarily make the end piece integral with the staple and to avoid a potential relative displacement during the application of the impact. In an even more preferred manner, said retaining lug 63 is threaded with a screw thread complementary to the tapping of the orifice 13 of the staple, such that it can be screwed into the staple. This embodiment is particularly advantageous for cases where it could be necessary to extract the staple from the vertebra into which it has been implanted to remove it or to modify its position, the tapped orifice 43 then remaining the only element for gripping the staple.

Figure 6A:
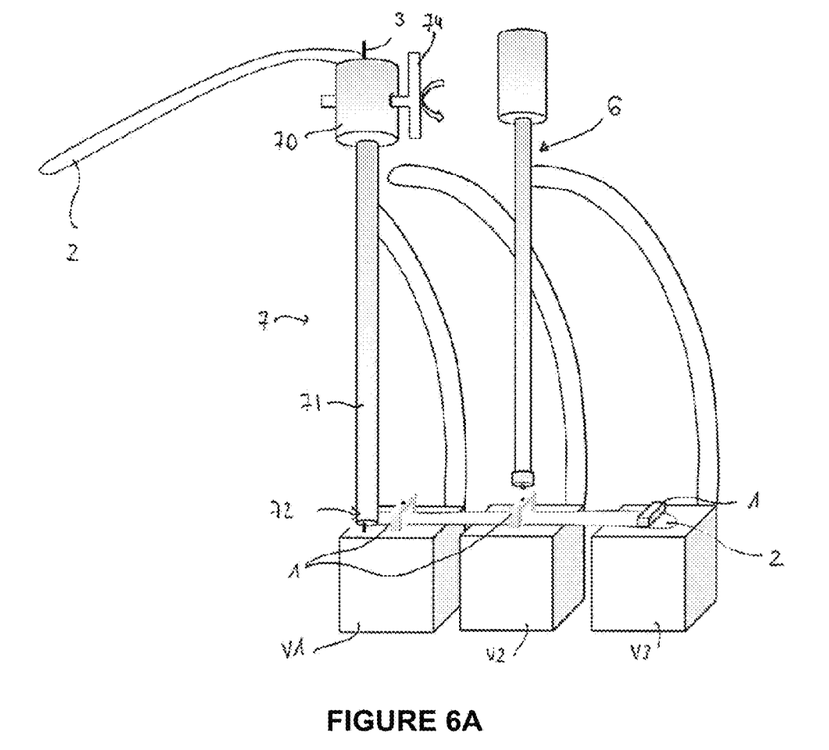
FIG. 6A is a schematic diagram of the tensioning of the ligament before the impaction of a staple.

FIG. 6A illustrates the situation of the correction device after the definitive putting in place of the staple 1 on the vertebra V3, thereby immobilising one end of the ligament 2. To apply a mechanical tension to the ligament (this mechanical tension being determined by the practitioner with regard to the correction to obtain), a novel ancillary specially designed for the invention is used, namely a device 7 for mechanically tensioning the ligament.

The device 7 comprises a tubular rod 71 for the passage of the ligament between a distal end 72 and a proximal end 70 of the rod. The internal diameter of the tube is advantageously slightly greater than the width of the ligament to enable the sliding thereof without torsion. Furthermore, the rod 71 being intended to be inserted into the body of the patient, it has an external diameter as small as possible, that is to say typically comprised between 8 and 10 mm.

Figure 6B:
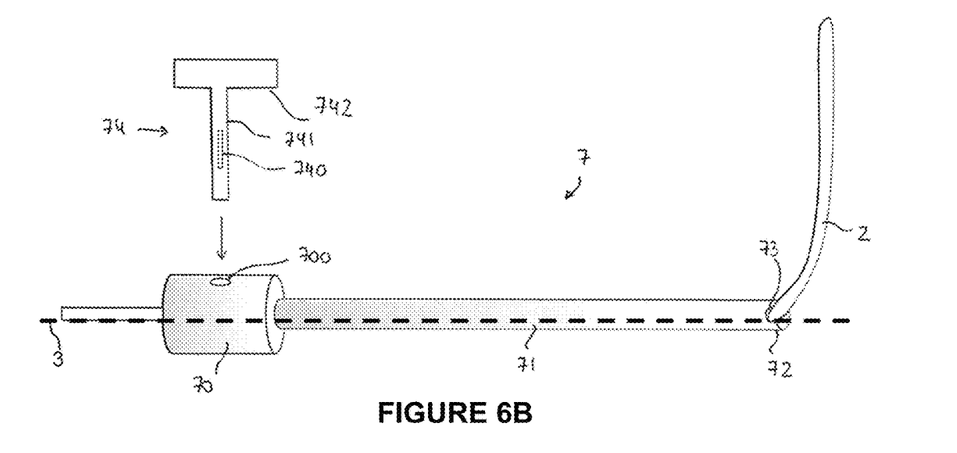
FIG. 6B is a schematic diagram of the device for tensioning the ligament.
Figure 6C:
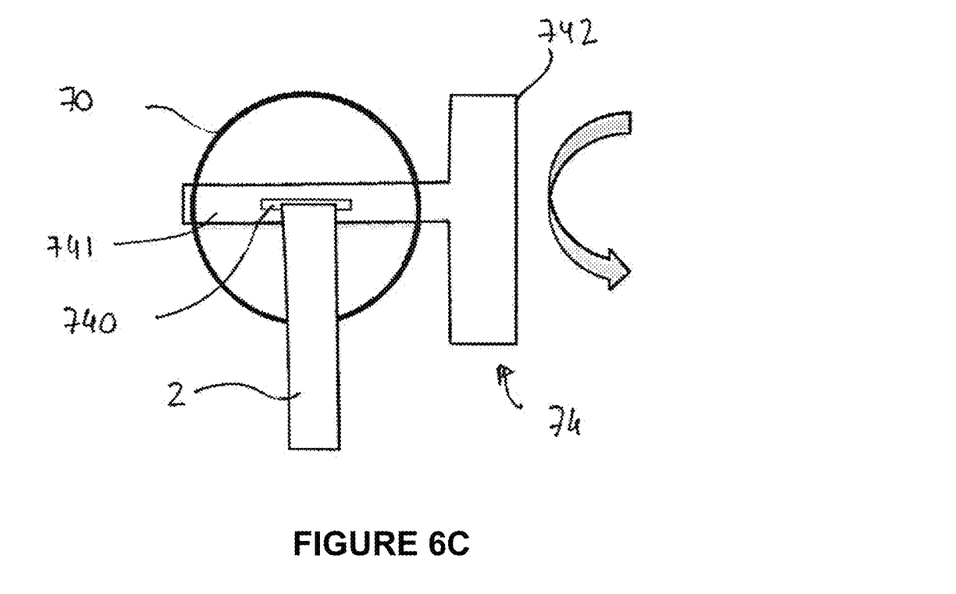
FIG. 6C is a principle view of a torque wrench arranged at the proximal end of the device for tensioning the ligament.
Figure 6D:
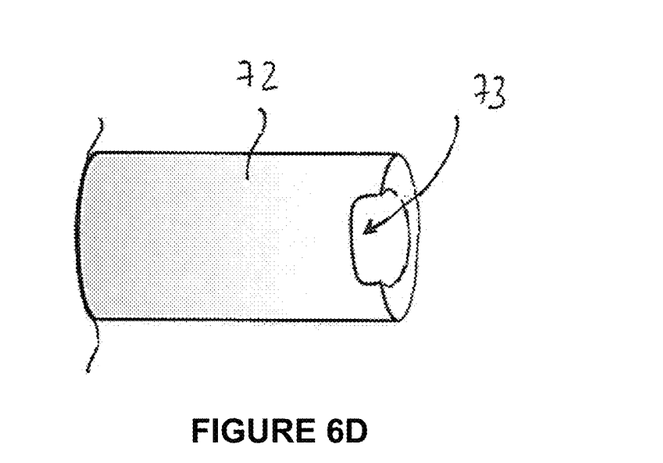
FIG. 6D is a principle view of the distal end of the device for tensioning the ligament.

As may be seen better in FIGS. 6B and 6D, at the distal end thereof 72, the rod 71 has a notch 73 arranged on a part of its circumference and in which emerges the passage for the ligament. The notch 73 typically has a width slightly greater than the width of the ligament 2 and a height slightly greater than the thickness of the ligament.

Furthermore, the device 7 comprises a torque wrench 74 arranged at the proximal end 70 of the rod 71. As may be seen better in FIG. 6C, said torque wrench comprises a spindle 741 that is perpendicular to the rod 71 and has a slit 740 through which the ligament 2 passes. The width of said slit 740 is thus substantially equal to that of the ligament. The spindle of the wrench 74 is suitable for being rotated in such a way as to adjust the mechanical tension of the ligament.

Returning to FIG. 6A, once a staple (here, that of the vertebra V3) has been put in place definitively, the distal end 72 of the device 7 is pressed onto a neighbouring vertebra (here, the vertebra V1) and a determined mechanical tension is applied by means of the device 7 to the portion of the ligament situated between said staple and an adjacent staple not yet put in place definitively (here, that of the vertebra V2). According to an advantageous embodiment, through the rod 71 is inserted a pin with a diameter of the order of 3 mm (for example a pin 3 having served to position the staple for its pre-implantation)—or even two pins of 3 mm diameter—penetrating superficially into the vertebra in order to stabilise the device 7 and to avoid any slippage of the distal end 72 along the length of the vertebra during the adjustment of the mechanical tension of the ligament. The internal diameter of the rod 71 is in fact sufficiently large to enable the passage at one and the same time of the ligament and one or two pins 3. The pin 3 has been represented in dotted lines in FIG. 6B. Thus, unlike the system described in the aforementioned U.S. Patent Publication No. 2013/0060287, the pin 3 makes it possible to maintain the device 7 against the vertebra without pressing it against the staple, which avoids applying stresses to the staple during tensioning of the ligament.

Once this tensioning has been obtained, the staple preimplanted on the vertebra V2 is definitively put in place by means of the second impaction device 6. All the staples are thereby put in place progressively, while adjusting beforehand the mechanical tension of the ligament. The practitioner may of course choose to apply a different mechanical tension between two different pairs of adjacent staples.

As appears from the description of the implantation procedure, the correction system implemented in the invention is really minimally invasive, that is to say that it only requires incisions less than 10 mm. Thus, putting the staples and the ligament in place only involves limited bleeding and enables rapid cicatrisation, which is favourable to good acceptance of this treatment. Once the staples and the ligament have been put in place, the correction is much less demanding for the patient than conventional corsets. In this respect, the invention may be likened to a corset internal to the patient. On the other hand, the correction system makes it possible to adjust precisely the mechanical tension of the ligament and thereby to improve the effectiveness of the correction. First results show a stabilisation of severe scolioses despite growth of the patient.

REFERENCES

[1] Growth modulation by means of anterior tethering resulting in progressive correction of juvenile idiopathic scoliosis: a case report. Crawford C H III, Lenke L G. J. Bone Joint Surg. Am. 2010; 92:202-9.
[2] Anterior vertebral body tethering for immature adolescent idiopathic scoliosis: one-year results on the first 32 patients. Samdani A F, Ames R J, Kimball J S, Pahys J M, Grewal H, Pelletier G J, Betz R R. Eur Spine J. 2014 Dec. 16.
[3] Anterior vertebral body tethering for idiopathic scoliosis: two-year results. Samdani A F, Ames R J, Kimball J S, Pahys J M, Grewal H, Pelletier G J, Betz R R. Spine (Phila Pa. 1976). 2014 Sep. 15; 39(20):1688-93.

The invention claimed is:

1. A minimally invasive system for dynamic correction of a spinal deformity in patients, the system comprising:
   a flat ligament made of synthetic material;
   a plurality of staples configured to be anchored on a respective vertebral body of the patient to hold the ligament against each vertebral body;
   a device configured to mechanically tension the ligament;
   wherein the device configured to mechanically tension the ligament comprising:
      a tubular rod configured to allow the ligament and at least one pin capable of penetrating the vertebral body so as to prevent slippage of the distal end of the rod on the vertebral body to pass between a distal end and a proximal end of the rod, the rod leading, at the distal end thereof, into a notch suitable for the ligament to pass through; and
      a torque wrench arranged at the proximal end of the rod, the torque wrench comprising a spindle that is perpendicular to the rod and has a slit through which the ligament passes, the spindle of the wrench being suitable for being rotated so as to adjust the mechanical tension of the ligament.
2. The system according to claim 1, wherein each staple includes:
   two substantially parallel pointed legs having a spacing designed to provide a passage for the ligament;
   a flange connecting the legs and having a tapped central orifice; and
   on a same side of the flange as the legs, at least one tip configured to perforate the ligament, the tip being shorter than the legs of the staple.
3. The system according to claim 2, wherein a thickness of the flange of each staple is comprised between 1 and 3 mm.
4. The system according to claim 2, further comprising at least one pin configured for guiding a sliding of the staple, the pin having a diameter substantially equal to a diameter of the central orifice of the staple.
5. The system according to claim 4, further comprising a first impaction device configured to impact the staple, said impaction device comprising a tubular rod enabling the guiding pin to pass through the impaction device.
6. The system according to claim 5, wherein the first impaction device has, at the distal end thereof, an end piece suited to engage with the flange of the staple in such a way as to orient the staple in a determined position.
7. The system according to claim 5, wherein at least one of: the part intended to be inserted into the body of the patient of the tensioning device, the first impaction device, a second impaction device and/or a gripper, has a diameter less than or equal to 10 mm.
8. The system according to one of claim 2, further comprising at least one gripper configured to grip the ligament, the gripper comprising two arms each having a distal end bent according to an angle comprised between 80 and 95° forming a jaw, the arms being able to be actuated between a configuration where the jaws are spaced apart and a configuration where the jaws are tightened against each other.
9. The system according to claim 8, wherein at least one of: the part intended to be inserted into the body of the patient of the tensioning device, a first impaction device, a second impaction device and/or the gripper, has a diameter less than or equal to 10 mm.
10. The system according to claim 2, further comprising:
    a first impaction device; and
    a second impaction device configured to impact the staple, the second impaction device having, at a distal end thereof, a retaining lug engaging with the central orifice of each staple.
11. The system according to claim 10, wherein the retaining lug is threaded and is configured to be screwed into the central orifice of each staple.
12. The system according to claim 10, wherein at least one of: the part intended to be inserted into the body of the patient of the tensioning device, the first impaction device, a second impaction device and/or a gripper, has a diameter less than or equal to 10 mm.
13. The system according to claim 1, wherein the ligament is in the form of a polyester braid.
14. The system according to claim 1, wherein the ligament comprises at least one radio-opaque element extending over the entire length of the ligament.

* * * * *